US009836030B2

(12) United States Patent
Takano et al.

(10) Patent No.: US 9,836,030 B2
(45) Date of Patent: Dec. 5, 2017

(54) PORTABLE ELECTRONIC DEVICE

(71) Applicant: Seiko Epson Corporation, Shinjuku-ku (JP)

(72) Inventors: Yuichi Takano, Matsumoto (JP); Naoshi Furuta, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 9 days.

(21) Appl. No.: 14/511,110

(22) Filed: Oct. 9, 2014

(65) Prior Publication Data
US 2015/0103632 A1 Apr. 16, 2015

(30) Foreign Application Priority Data

Oct. 11, 2013 (JP) .................................. 2013-213397

(51) Int. Cl.
G04G 19/00 (2006.01)
A61B 5/024 (2006.01)
A61B 5/00 (2006.01)

(52) U.S. Cl.
CPC ......... *G04G 19/00* (2013.01); *A61B 5/02438* (2013.01); *A61B 5/681* (2013.01); *A61B 2560/029* (2013.01); *A61B 2560/0214* (2013.01); *A61B 2560/0456* (2013.01)

(58) Field of Classification Search
CPC .................................................... G04G 19/00
USPC ........................................................ 320/149
See application file for complete search history.

(56) References Cited

U.S. PATENT DOCUMENTS

| 6,042,549 A | 3/2000 | Amano et al. |
| D640,977 S | 7/2011 | Videbaek |
| 2008/0285780 A1 | 11/2008 | Aarts |
| 2009/0040877 A1* | 2/2009 | McGeough ............ G04G 11/00 368/73 |
| 2010/0081947 A1* | 4/2010 | Suzuki ................... A61B 5/024 600/500 |
| 2011/0050447 A1* | 3/2011 | Tedesco ............. G08B 13/1427 340/687 |
| 2011/0077551 A1 | 3/2011 | Videbaek |
| 2012/0215115 A1* | 8/2012 | Takahashi .......... A61B 5/02416 600/483 |

(Continued)

FOREIGN PATENT DOCUMENTS

| JP | 2008-241329 A | 10/2008 |
| JP | 2009-514313 A | 4/2009 |

(Continued)

*Primary Examiner* — Drew A Dunn
*Assistant Examiner* — Jerry D Robbins
(74) *Attorney, Agent, or Firm* — Kilpatrick Townsend & Stockton LLP

(57) ABSTRACT

A portable electronic device (biological information measurement device) is attachable to or detachable from a cradle and includes a USB terminal portion connected to a terminal provided in the cradle, an initial start-up unit that initially starts up the biological information measurement device, a connection determination unit that determines whether the connection has been released after the USB terminal portion has been connected to a terminal portion of the cradle, and a resetting unit that causes the initial start-up unit to initially start up the biological information measurement device when it is determined by the connection determination unit that the connection has been released after the cradle has been connected to the USB terminal portion.

7 Claims, 8 Drawing Sheets

(56) References Cited

U.S. PATENT DOCUMENTS

| | | | | |
|---|---|---|---|---|
| 2012/0245439 A1* | 9/2012 | Andre | .................. | A61B 5/0205 |
| | | | | 600/310 |
| 2012/0316456 A1* | 12/2012 | Rahman | .................. | G06F 1/163 |
| | | | | 600/547 |
| 2013/0006123 A1* | 1/2013 | Aoshima | ............ | A61B 5/02438 |
| | | | | 600/483 |
| 2014/0018686 A1* | 1/2014 | Medelius | .............. | A61B 5/7203 |
| | | | | 600/483 |
| 2014/0062405 A1 | 3/2014 | Videbaek | | |
| 2014/0249853 A1* | 9/2014 | Proud | .................... | G06Q 50/24 |
| | | | | 705/3 |
| 2014/0357960 A1* | 12/2014 | Phillips | .................. | A61B 5/486 |
| | | | | 600/301 |
| 2015/0332031 A1* | 11/2015 | Mistry | .................. | G06F 21/316 |
| | | | | 726/19 |

FOREIGN PATENT DOCUMENTS

| | | | | |
|---|---|---|---|---|
| JP | 2012-526596 A | 11/2012 | | |
| JP | 2013-505774 A | 2/2013 | | |
| JP | 2013-085612 A | 5/2013 | | |
| KR | 1020110123898 A | * 11/2011 | ................ | H02J 7/00 |
| WO | 97-35514 A1 | 10/1997 | | |

\* cited by examiner

PORTABLE ELECTRONIC DEVICE

BACKGROUND

1. Technical Field

The present invention relates to a portable electronic device that is attachable to or detachable from a cradle.

2. Related Art

In a small portable electronic device such as a timepiece, disturbances such as noise or static electricity intruding from the outside may be often transferred to an internal circuit board, and may cause a malfunction of an internal electronic circuit. Therefore, an electronic circuit for a timepiece capable of performing system resetting to reset a state of the system is known (for example, JP-A-2008-241329).

An electronic circuit for a timepiece described in JP-A-2008-241329 includes a first storage unit that stores various operation programs and an operation program for a resetting operation, a second storage unit that stores key assignment information for the resetting operation for resetting a function of the timepiece, and an input circuit, in which information input from the input circuit and the key assignment information are compared, the operation program for a resetting operation stored in the first storage unit is called to execute the resetting operation of the timepiece when the input information and the key assignment information match ([0026] to [0036] of JP-A-2008-241329).

However, in the timepiece with the electronic circuit for a timepiece described in JP-A-2008-241329, system resetting cannot be performed if a user does not operate an operation unit provided in the timepiece by himself or herself. Therefore, if the user himself or herself does not intend to perform system resetting, the system resetting of the timepiece (portable electronic device) is not performed.

In other words, it is necessary to perform periodical system resetting of the portable electronic device in order to achieve stability of the system. When the user forgets the execution of a system resetting process, there is a problem in that the stability of the system cannot be maintained.

SUMMARY

An advantage of some aspects of the invention is that a portable electronic device capable of further maintaining stability of a system by executing a system resetting process through a task performed on a daily basis by a user is provided.

An aspect of the invention is directed to a portable electronic device that is attachable to or detachable from a cradle, the device including a connection portion connected to a terminal provided in the cradle; an initial start-up unit that initially starts up the portable electronic device; a connection determination unit that determines whether the connection has been released after the connection portion has been connected to the terminal of the cradle; and a resetting unit that causes the initial start-up unit to initially start up the portable electronic device when it is determined by the connection determination unit that the connection has been released. In addition, the initial start-up stated herein refers to not only turning-on of the portable electronic device for the first time, but also system resetting performed during use of the portable electronic device by a user, or an operation of transitioning from a power ON state to a power OFF state and then to the power ON state.

With this configuration, when the portable electronic device is attached to the cradle to connect the connection portion of the portable electronic device to the terminal of the cradle and then the portable electronic device is removed from the cradle to release the connection between the connection portion and the terminal of the cradle, the portable electronic device is initially started up.

Usually, the attachment of the portable electronic device to the cradle is periodically performed, for example, once a day to charge the portable electronic device or to exchange various information with the other electronic device (for example, a personal computer) connected to the cradle. Therefore, if initialization (system resetting) of the portable electronic device is executed by a task performed on a daily basis by the user, such as removal of the portable electronic device from the cradle, the system resetting can be automatically executed even when the user does not intentionally perform the system resetting operation. Therefore, since the portable electronic device can be periodically subjected to system resetting, the stability of the system can be improved in comparison with the case in which system resetting is not performed for a long period of time.

In the portable electronic device of the aspect of the invention, it is preferable that the portable electronic device further includes a rechargeable battery, the connection portion includes a charging connection portion that acquires power that is supplied from the cradle, and the connection determination unit detects a voltage or a current applied to the charging connection portion and determines whether the connection to the terminal of the cradle has been released.

With this configuration, the voltage or the current applied to the charging connection portion is detected to determine whether the connection to the terminal of the cradle has been released. For example, the voltage or the current of the charging connection portion increases when the charging connection portion is connected to the terminal of the cradle, and decreases when the connection is released. Thus, if a change in the voltage or the current applied to the charging connection portion is detected and the system resetting is automatically performed, the system resetting can be executed each time the portable electronic device is charged. Therefore, even when the connection portion is connected to the terminal of the cradle, power is not supplied to the cradle, for example, if the cradle is not connected to another electronic device. Thus, the system resetting is not performed. In other words, since it is usually necessary to charge the battery provided in the portable electronic device at constant intervals (for example, every day), the user necessarily sets the portable electronic device in the cradle in order to perform charging of the portable electronic device. Also, when charging is completed, the portable electronic device is removed from the cradle. Therefore, even when the user does not perform a system resetting operation, the system resetting can be executed automatically at the time of a charging task executed on a daily basis.

In the portable electronic device of the aspect of the invention, it is preferable that the connection portion includes an information exchange connection portion that exchanges information with another electronic device connected to the cradle via the cradle, and the connection determination unit detects a result of the information exchange via the information exchange connection portion and determines whether the connection to the terminal of the cradle has been released.

With this configuration, when the information exchange (communication process) fails after the information exchange is successful as a result of the information exchange via the information exchange connection portion, it can be determined that the connection of the connection portion connected to the terminal of the cradle has been released. In addition, when a charging connection terminal is not provided in the cradle, it can be determined that the connection has been released.

In the portable electronic device of the aspect of the invention, it is preferable that the portable electronic device further includes a display unit; a plurality of light emitting elements; a pulse acquisition unit that acquires a pulse rate of a subject; a pulse zone determination unit that determines any one of a plurality of pulse zones divided in advance to which the pulse rate belongs; and a report control unit that reports the pulse zone to which the pulse rate belongs by controlling a lighting state of the plurality of light emitting elements based on a determination result of the pulse zone determination unit.

With this configuration, the pulse zone determination unit determines any one of the plurality of pulse zones to which the pulse rate acquired by the pulse acquisition unit belongs. Also, the report control unit reports the determined pulse zone by controlling the lighting state of the plurality of light emitting elements. For example, when the pulse zones are divided into four steps from the first zone of a low pulse rate to a fourth zone of a high pulse rate, one light emitting element blinks if the pulse rate acquired by the pulse acquisition unit belongs to the first zone, two light emitting elements blink if the pulse rate belongs to the second zone, three light emitting elements blink if the pulse rate belongs to the third zone, and four light emitting elements blink if the pulse rate belongs to the fourth zone, to report the determined pulse zone.

Therefore, a subject or a manager managing a state of the subject (hereinafter collectively referred to as a user) can easily recognize the pulse zone to which a current pulse rate belongs, based on the lighting state of the plurality of light emitting elements. Particularly, if the lighting state is controlled to change the number of light emitting elements that are lit according to a level of the pulse zone, it is possible to easily recognize the pulse zone to which the pulse rate belongs. In addition, since the lighting state of the light emitting elements is controlled, the user can reliably recognize the determined pulse zone even at night.

Here, the plurality of pulse zones divided in advance are a plurality of zones obtained by dividing a target range of pulse rates (for example, 80 times/m to 140 times/m) for exercise or the like for a subject in advance (by, for example, 15 times/m).

Accordingly, since the user can recognize the current pulse zone from the lighting state of the light emitting elements, it can be easily determined whether current exercise strength is to be maintained or changed.

In addition, since various information such as the measured pulse rate can be communicated with the other electronic device via the cradle 9, measurement data can be analyzed in detail in a personal computer or the like. Further, since the pulse zones can be set in the personal computer or the like and set data can be transmitted to the portable electronic device via the cradle 9, it is unnecessary for the portable electronic device to perform a task of setting the pulse zones or the like and a burden of tasks of the user can be reduced.

In the portable electronic device of the aspect of the invention, it is preferable that the portable electronic device further includes an exercise evaluation amount measurement unit that measures an exercise evaluation amount for evaluating an exercise amount of the subject; and an achievement degree evaluation unit that evaluates a degree of achievement of the exercise evaluation amount with respect to a target exercise value set in advance, in which when the pulse zone is reported, the report control unit reports the achievement degree evaluated by the achievement degree evaluation unit by controlling the lighting state of the plurality of light emitting elements when an operation of instructing a report is performed by the subject.

With this configuration, the exercise evaluation amount for evaluating an exercise amount of the subject is measured. This exercise evaluation amount may include a calorie consumption amount caused by the exercise of the subject, an exercise time, the number of steps, etc. In addition, if the pulse zone corresponding to the pulse rate is reported, the achievement degree for the target value is reported based on the lighting state of the plurality of light emitting elements only when the user performs an operation of instructing a report, the current pulse zone and the target achievement degree can be compared. Accordingly, the user can easily determine whether to maintain, increase, or decrease the own exercise amount and pulse rate (exercise strength) based on the achievement degree for the target set in advance. Therefore, it is possible to perform more efficient exercise support.

In addition, since various information such as the measured exercise evaluation amount can be communicated with the other electronic device via the cradle 9, it is possible to analyze measurement data in detail in a personal computer or the like. Further, since the target value or the like can be set in the personal computer or the like and set data can be transmitted to the portable electronic device via the cradle 9, it is unnecessary for the portable electronic device to perform a task of setting the target value or the like, and a burden of tasks of the user can be reduced.

In the portable electronic device of the aspect of the invention, it is preferable that the portable electronic device further includes a rechargeable battery, the connection portion includes a charging connection portion that acquires power supplied from the cradle, and the report control unit controls at least one of the plurality of light emitting elements to be in a lighting state when the power supplied from the cradle via the charging connection portion is supplied to the battery.

With this configuration, when the power supplied from the cradle via the charging connection portion is supplied to the battery, that is, the battery is being charged, at least one of the plurality of light emitting elements is lit and thus it is possible to easily recognize that the portable electronic device is being charged. In addition, when at least one of the plurality of light emitting elements is not lit even though the portable electronic device and the cradle are connected, the user can recognize that the portable electronic device cannot be charged and, for example, that the cradle is not connected to the other electronic device. Therefore, it is possible to reliably charge the portable electronic device.

In the portable electronic device of the aspect of the invention, it is preferable that the portable electronic device further includes a rechargeable battery; and a charge amount determination unit that determines whether a charge amount of the battery is less than a predetermined charge amount, and the report control unit causes the display unit to display information for urging charging when it is determined by the charge amount determination unit that the charge amount of the battery is less than the predetermined charge amount.

With this configuration, when the charge amount of the battery is less than a predetermined charge amount, information for urging charging is displayed on the display unit. Therefore, it is possible to urge a user to charge the portable electronic device. Accordingly, the user can perform charging of the portable electronic device more reliably, such that system resetting is automatically performed each time the charging is performed, and the stability of the system can be further maintained.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, a biological information measurement device that is an embodiment of the portable electronic device according to the invention and a cradle attached to the biological information measurement device will be described based on the drawings.

Entire Configuration of the Biological Information Measurement Device

Figure 1:
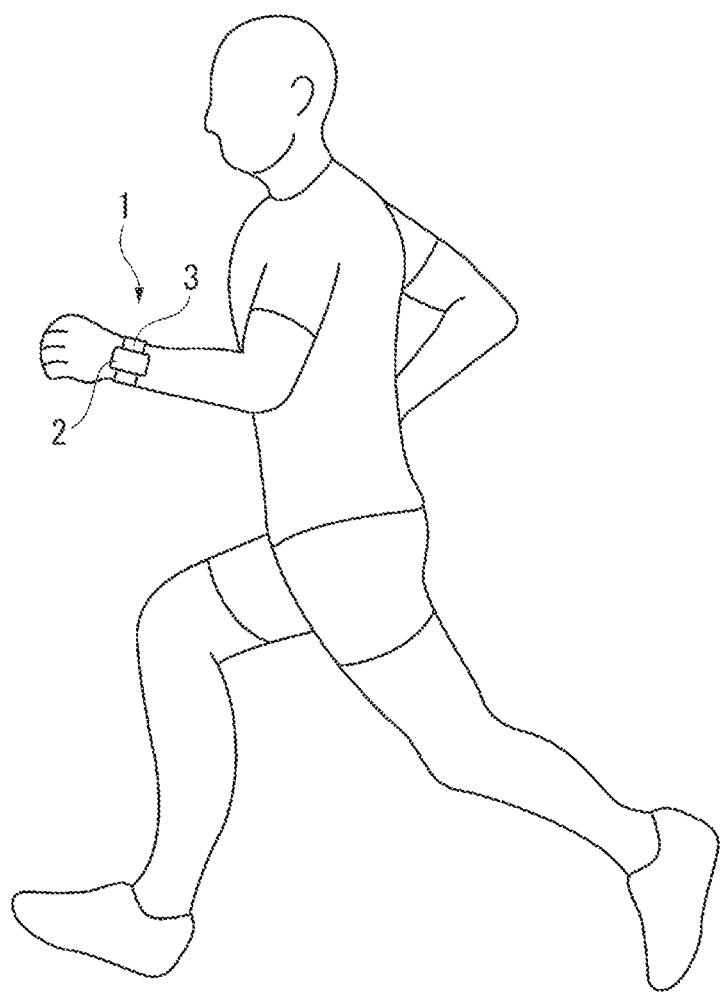
FIG. 1 is a diagram illustrating a schematic biological information measurement device of the embodiment.

FIG. 1 is a diagram illustrating a schematic biological information measurement device 1 of a first embodiment.

As illustrated in FIG. 1, the biological information measurement device 1 of the embodiment is attached to, for example, a wrist of a user (subject), detects a pulse of the user to calculate a pulse rate per unit time (usually, 1 minute), and outputs exercise support information indicating any one of a plurality of pulse zones set in advance to which the pulse rate corresponds. In addition, the output exercise support information is output based on a lighting state of a light emitting diode (LED) light source unit 7 that is a light emitting element provided in the biological information measurement device 1, which will be described below.

Figure 2:
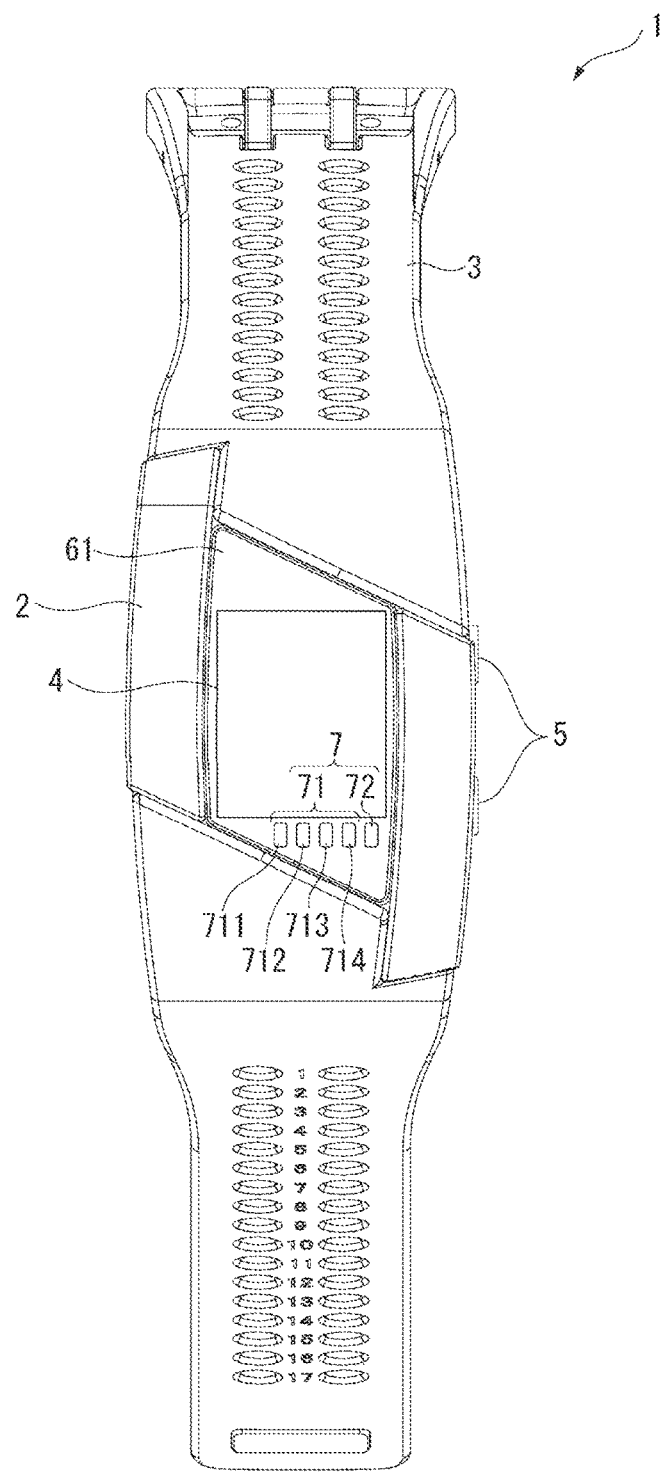
FIG. 2 is a front view illustrating a surface side of the biological information measurement device of the embodiment.
Figure 3:
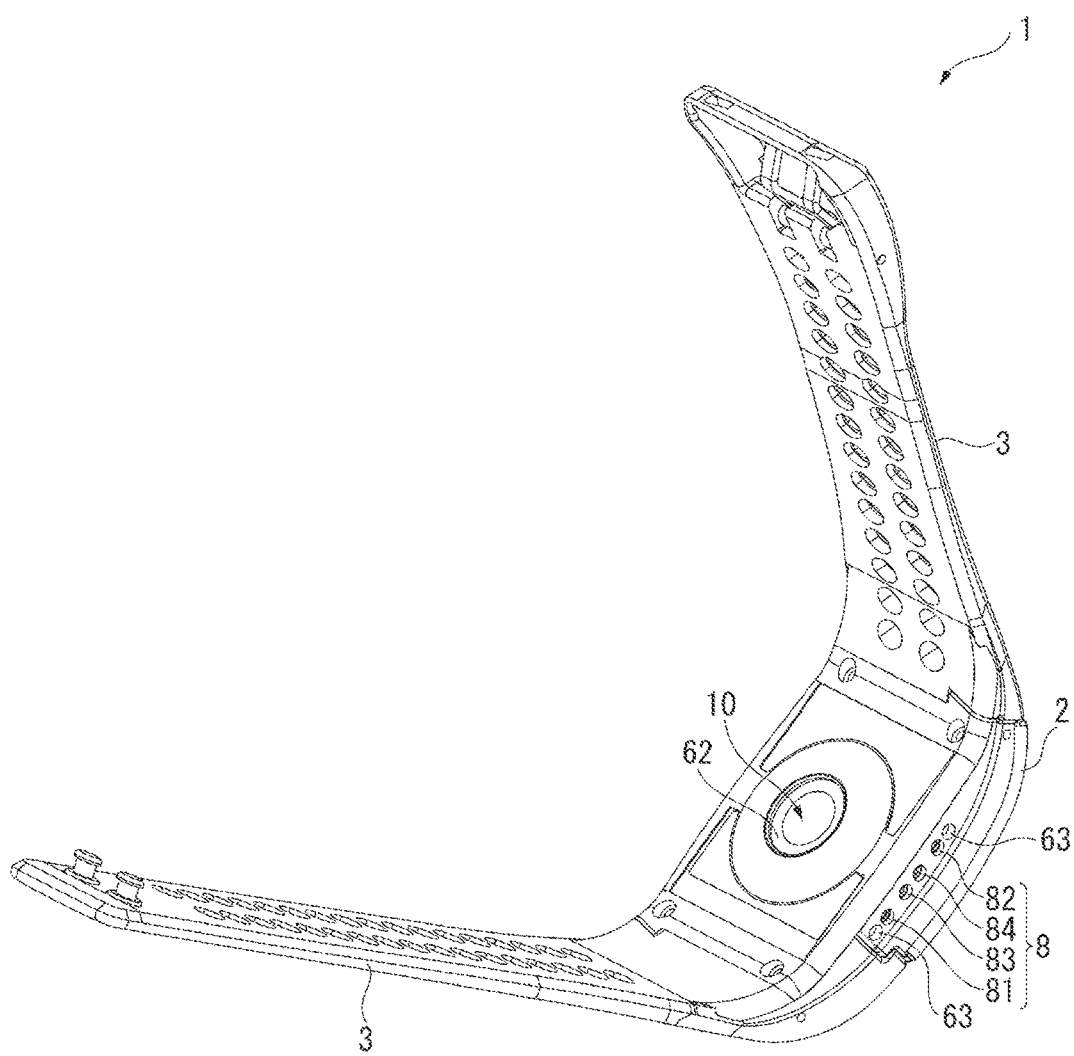
FIG. 3 is a perspective view illustrating a back surface side of the biological information measurement device of the embodiment.
Figure 4:
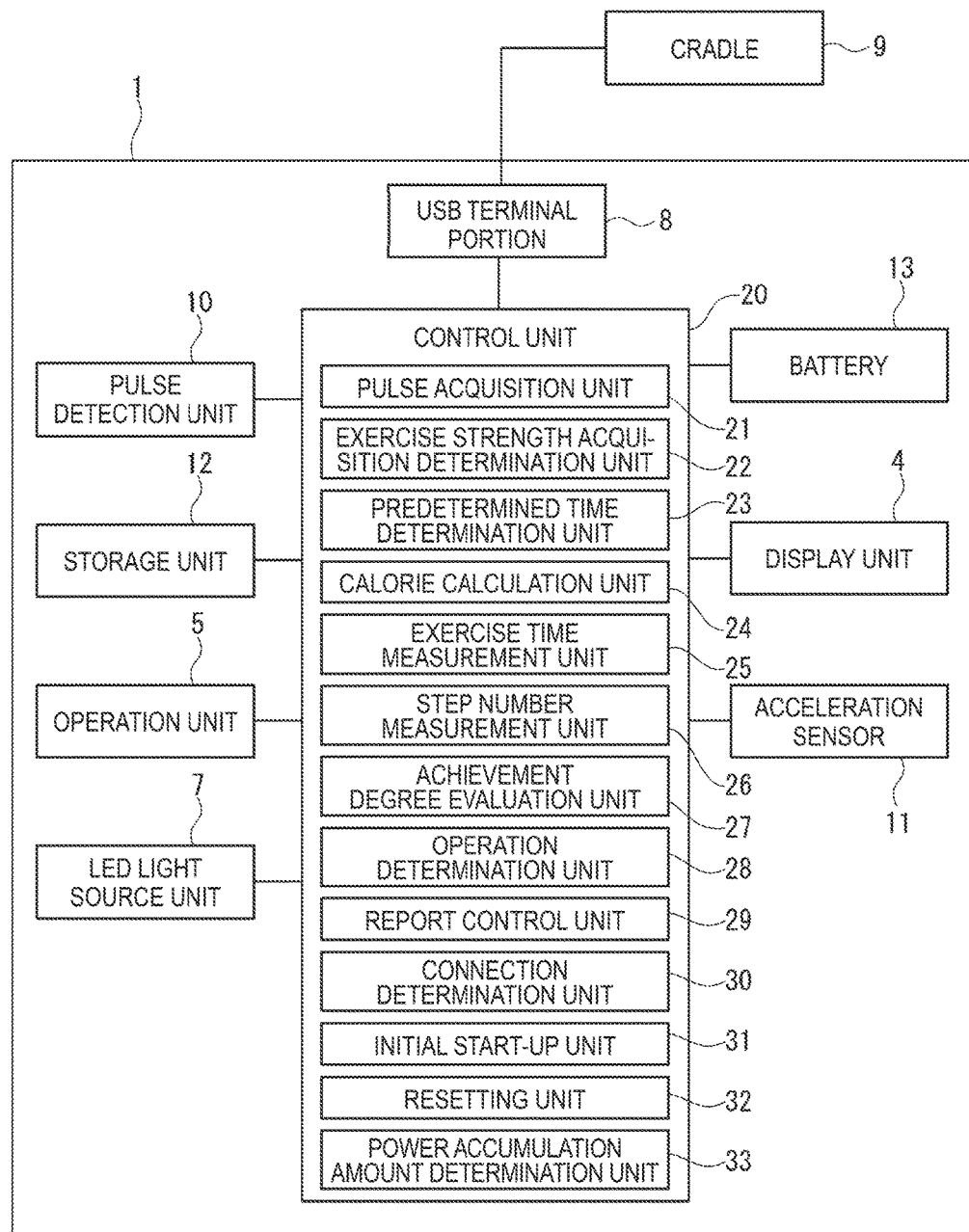
FIG. 4 is a block diagram illustrating a schematic configuration of the biological information measurement device of the embodiment.

FIG. 2 is a front view illustrating the biological information measurement device 1. FIG. 3 is a perspective view illustrating a back surface side of the biological information measurement device 1. FIG. 4 is a block diagram illustrating a schematic configuration of the biological information measurement device 1.

The biological information measurement device 1 includes a device body 2, and a band 3 connected to the device body 2, as illustrated in FIGS. 2 and 3. Also, this biological information measurement device 1 may be attached to a living body by tightening the band 3 in a state in which a back surface is adhered to the living body, monitor a state of a blood flow flowing in a blood vessel, and measure a pulse.

A display unit 4 that displays various information such as a measurement result of a pulse rate or the like, and an LED light source unit 7 that reports exercise support information (for example, exercise strength) are provided on the surface side of the device body 2 of the biological information measurement device 1, as illustrated in FIGS. 2 and 3. The LED light source unit 7 includes a plurality of first light emitting elements 71 that are lit green, and a second light emitting element 72 that is lit orange. The plurality of first light emitting elements 71 include four first light emitting elements 711, 712, 713 and 714. The first light emitting elements 711, 712, 713 and 714 and the second light emitting element 72 are arranged in series in one direction, and the second light emitting element 72 is arranged in the farthest end portion. The display unit 4 and the LED light source unit 7 are both covered by a transparent member 61, such as glass or plastic.

In addition, the lighting colors of the plurality of first light emitting elements 71 and the second light emitting element 72 are not limited to the green and the orange. The lighting colors of the plurality of first light emitting elements 71 and the second light emitting element 72 may be any colors as long as the colors are different. However, it is preferable for the first light emitting elements 71 to have a color reminding the user of a normal state, such as blue or green, in order to show a normal state. On the other hand, it is preferable for the second light emitting element 72 to have a color calling the user's attention, such as red, yellow, or orange, so that the second light emitting element 72 is lit when the attention is called. In addition, arrangement of the plurality of first light emitting elements 71 and the second light emitting element 72 is not limited to a straight line in one direction. The plurality of first light emitting elements 71 and the second light emitting element 72 may be arranged in an arc according to a shape of the device body 2.

Operation units 5 for operating the biological information measurement device 1 are provided on one side surface of the device body 2, as illustrated in FIGS. 2 and 3. In addition, a universal serial bus (USB) terminal portion 8 connected to a terminal portion 94 of the cradle 9 (see FIG. 5) is provided on the other side surface of the device body 2, as illustrated in FIG. 4. The USB terminal portion 8 of the biological information measurement device 1 and the terminal portion 94 of the cradle 9 correspond to a standard of USB 2.0. Two of four connection terminals are a $V_{BUS}$ terminal and a GND terminal for power supply, and the other two terminals are terminals for data communication.

In other words, although to be described in detail below, the terminal portion 94 of the cradle 9 includes four connection terminals, including a $V_{BUS}$ terminal 941, a GND terminal 942, a D+ terminal 943, and a D− terminal 944 (see FIG. 5). The $V_{BUS}$ terminal 941 and the GND terminal 942 are used for power supply, and the D+ terminal 943 and the D− terminal 944 are used for information transfer to exchange various information. Therefore, the USB terminal portion 8 includes a $V_{BUS}$ terminal 81 and a GND terminal 82 as a charging connection portion connected to the $V_{BUS}$ terminal 941 and the GND terminal 942, and a D+ terminal 83 and a D− terminal 84 as an information exchange connection portion connected to the D+ terminal 943 and the D− terminal 944.

In addition, positioning holes 63 for performing positioning when the device body 2 is connected to the cradle 9 are provided on the both end sides of the USB terminal portion 8.

The cradle 9 is connected to a personal computer via a USB terminal 99. Also, when the biological information measurement device 1 is attached to the cradle 9 connected to the personal computer, power is supplied from the $V_{BUS}$ terminal 941 and the GND terminal 942 provided in this cradle 9, making it possible to charge the biological information measurement device 1. In addition, the USB terminal portion 8 and the terminal portion 94 of the cradle 9 are connected, making it possible to acquire (exchange) various information (for example, a target exercise value or physical information) from another electronic device (for example, a personal computer or a smartphone) used integrally with the cradle 9 via the D+ terminal 943 and the D− terminal 944.

In addition, in the embodiment, the configuration in which the USB terminal portion 8 and the terminal portion 94 of the cradle 9 are connected to acquire various information (for example, target exercise value or physical information) from the cradle 9 is illustrated, but the invention is not limited thereto. For example, a configuration in which the biological information measurement device 1 includes a wireless communication device such as Bluetooth (registered trademark), is connected with the cradle 9 to be able to perform wireless data communication, and acquires various information may be adopted. In other words, at least a charging connection portion may be provided in the biological information measurement device 1, and a terminal portion connected to the charging connection portion and supplying power to the biological information measurement device 1 may be provided in the cradle 9.

A transparent window 6 is formed on the back surface side of the device body 2, and a pulse detection unit 10 is arranged on the backside (on the inside side of the device body 2) of this window 6, as illustrated in FIG. 3.

The pulse detection unit 10 includes, for example, a photoelectric sensor including a light emitting element such as an LED, and a light receiving element such as a photodiode. In this pulse detection unit 10, light is radiated from the light emitting element to the living body in a state in which the biological information measurement device 1 is attached to a wrist. A change in a light amount when light arriving via a blood vessel of the living body is received by the light receiving element is detected to detect a pulse wave. In other words, the light radiated to the living body is partially absorbed into the blood vessel, but an absorption factor in this blood vessel is changed under an influence of a heartbeat and an amount of light arriving at the light receiving element is changed. Also, a temporal change of the light amount detected by the light receiving element, that is, a pulse wave is analyzed such that a pulse rate can be measured.

In addition, in the embodiment, while an example in which the photoelectric sensor is used as the pulse detection unit 10 has been shown, for example, an ultrasonic wave sensor that detects shrinkage of the blood vessel using an ultrasonic wave and measures a pulse rate may be used, or a sensor, a piezoelectric element or the like that flows weak current from an electrode into a body and detects a pulse may be used.

An acceleration sensor 11, a storage unit 12, a battery 13 and a control unit 20 are provided inside the device body 2, as illustrated in FIG. 4.

The acceleration sensor 11 detects acceleration due to an operation of the user. The detected acceleration is output to the control unit 20. In the control unit 20, the number of steps or the like is calculated from the detected acceleration. In addition, in the embodiment, while an example in which the acceleration sensor 11 is provided to calculate the number of steps is shown, for example, a configuration in which a pendulum vibrating according to a walking operation of the user is included and the number of steps is measured based on the number of vibrations of the pendulum may be adopted.

The storage unit 12 includes, for example, a Read Only Memory (ROM), a Random Access Memory (RAM), or a flash memory, and stores various data. Particularly, a flash memory that is a nonvolatile memory which is rewritable and from which data is not deleted even when power is switched off is used such that measured data is not deleted even when a system resetting operation is performed.

The various data include, for example, measurement data such as the pulse rate detected by the pulse detection unit 10 or the number of steps calculated by the control unit 20 based on the acceleration sensor 11, user data such as an age of the user who uses the biological information measurement device 1, and various information acquired from the cradle 9.

The battery 13 is a rechargeable secondary battery, and is charged by the power supplied from the terminal portion 94 of the cradle 9.

The control unit 20 includes, for example, a CPU (Central Processing Unit), and functions as a pulse acquisition unit 21, an exercise strength acquisition and determination unit 22, a predetermined time determination unit 23, a calorie calculation unit 24 (an exercise evaluation amount measurement unit), an exercise time measurement unit 25 (an exercise evaluation amount measurement unit), a step number measurement unit 26 (an exercise evaluation amount measurement unit), an achievement degree evaluation unit 27, an operation determination unit 28, a report control unit 29, a connection determination unit 30, an initial start-up unit 31, a resetting unit 32, and a charge amount determination unit 33 by reading and executing a program stored in the storage unit 12, as illustrated in FIG. 4.

In addition, the control unit 20 includes an internal timer that measures time.

The pulse acquisition unit 21 acquires the pulse rate of the user based on a detection signal input from the pulse detection unit 10. In addition, the pulse acquisition unit 21 sequentially stores the acquired pulse rate in the storage unit 12.

The exercise strength acquisition and determination unit 22 has a plurality of pulse zones set therein, and determines the pulse zone to which the pulse rate acquired by the pulse acquisition unit 21 belongs. Therefore, the exercise strength acquisition and determination unit 22 constitutes pulse zone determination unit according to the invention.

When the pulse rate does not belong to any pulse zone, the exercise strength acquisition and determination unit 22 determines whether the pulse rate is higher than an upper limit value of the pulse zone or is lower than a lower limit value.

In addition, since the pulse rate is mainly changed in response to exercise strength, a determination of the zone to which the pulse rate belongs is a determination of a zone to which the exercise strength corresponding to the pulse rate belongs.

When the exercise strength determined by the exercise strength acquisition and determination unit 22 is out of the zones, the predetermined time determination unit 23 determines whether a time during which the exercise strength is out of the zones exceeds a predetermined time.

Here, the pulse zones to determine the pulse rate (exercise strength) will be described in detail.

In the embodiment, zones (pulse zones in the invention) to which the exercise strengths corresponding to the pulse rates belong are set in advance. In this case, the zones may be set for individuals based on various information, such as a height, weight, age, sex, and presence or absence of exercise experience of users, in consideration of there being an individual difference in pulse rate increase or decrease tendency. For example, an exercise strength zone is set to a range in which fat burning efficiency increases when the user exercises at the exercise strength that is within the range. In addition, this zone is divided into four zones (four pulse zones) of a first zone, a second zone, a third zone, and a fourth zone to correspond to the number (four) of first light emitting elements 71, and the fat burning efficiency is different among exercise strengths corresponding to the respective pulse zones. In this case, a pulse rate lower than that of the first zone unit exercise of strength insufficient to burn fat, and a pulse rate higher than that of the fourth zone unit exercise of exercise strength unnecessarily high to burn fat, i.e., exercise with low efficiency.

In addition, the setting of the pulse zones is not limited thereto and, for example, the pulse zones may be set to correspond to a pulse rate calculated using a Maffetone method or a Karvonen method. In addition, desired zones may be set by an operation of the operation unit 5 of the user.

The calorie calculation unit 24 (an exercise evaluation amount measurement unit) calculates a calorie consumption amount, which is one of the exercise evaluation amounts in the invention, from the pulse rate stored in the storage unit 12.

The exercise time measurement unit 25 (an exercise evaluation amount measurement unit) measures time in the zone, which is one of the exercise evaluation amounts in the invention, based on time of the internal timer.

The step number measurement unit 26 (an exercise evaluation amount measurement unit) counts steps of the user, which is one of the exercise evaluation amounts in the invention, based on the acceleration measured by the acceleration sensor 11.

The achievement degree evaluation unit 27 evaluates a ratio of each exercise evaluation amount to each target exercise value, that is, an achievement degree, using the calorie consumption amount, the exercise time and a total number of steps that are the exercise evaluation amounts measured by the calorie calculation unit 24, the exercise time measurement unit 25, and the step number measurement unit 26, and, for example, a target calorie consumption value, a target time value and a target number of steps that are target exercise values set by the user in advance.

In addition, various target exercise values may be directly input via the operation unit 5 by the user or may be acquired from the cradle 9 via the USB terminal portion 8. In addition, the various target values may be acquired from an external device through, for example, short range wireless communication.

The operation determination unit 28 determines whether there has been an operation of the operation unit 5 by the user. In addition, the operation determination unit 28 determines whether there has been a tapping operation of tapping the device body 2 based on a detection value of the acceleration sensor 11.

In addition, the report control unit 29 controls lighting (blinking) of the LED light source unit 7 based on various conditions to report the exercise strength described above.

Here, report control by the report control unit 29 will be described in detail. When it is determined by the operation determination unit 28 that there has been an operation of instructing a report, the report control unit 29 reports the exercise strength, and the degree (target achievement degree) of calorie consumption, the exercise time, and the number of steps with respect to the target exercise value evaluated by the achievement degree evaluation unit 27 described above, through control of lighting of the LED light source unit 7 (the plurality of first light emitting elements 71 and the second light emitting element 72).

For example, when the exercise strength is to be reported by the report control unit 29, the report control unit 29 selects the light emitting element to blink among the plurality of first light emitting elements 711 to 714 based on each zone to which the exercise strength belongs, and blinks the light emitting element. More specifically, when it is determined that the exercise strength corresponding to the pulse rate acquired by the pulse acquisition unit 21 belongs to the first zone, only the first light emitting element 711 arranged in a position farthest from the second light emitting element 72 is controlled to be in a lit state, and when it is determined that the exercise strength belongs to the second to fourth zones, the two to four first light emitting elements 712, 713 and 714 are controlled to be in a lit state sequentially from the first light emitting element 711 arranged in the position farthest from the second light emitting element 72 among the plurality of first light emitting elements 71. In other words, each time the exercise strength exceeds each zone, the number of the first light emitting elements 712, 713 and 714 that enter a blinking state gradually from the first light emitting element 711 arranged in the position farthest from the second light emitting element 72 among the plurality of first light emitting elements 71 is increased. Thus, since the number of first light emitting elements 711 to 714 controlled to be in a lit state is increased as the exercise strength increases, the zone to which the exercise strength of the subject belongs can be recognized in a sense by viewing a so-called digital level indication meter.

In addition, when the exercise strength exceeds an upper limit value of the pulse zone (an upper limit value of the fourth zone), all of the plurality of first light emitting elements 71 and the second light emitting element 72 enter a blinking state. Therefore, particularly, since the second light emitting element 72 lit with a second color is controlled to be a lit state, for example, an exercise state of the subject can be easily recognized to be excessive (overworked) (not in the range of the target exercise strength).

On the other hand, when the exercise strength is below a lower limit value of the pulse zone (a lower limit value of the first zone) (below the zone), the first light emitting element 711 arranged in the position farthest from the second light emitting element 72 among the plurality of first light emitting elements 71 blinks at second intervals longer than the first interval (for example, at intervals of 2 seconds). Accordingly, the user can easily recognize that the pulse rate (exercise strength) is below the lower limit value from a change in the blinking interval.

For example, when the target achievement degree is to be reported by the report control unit 29, the report control unit 29 selects the light emitting elements to be lit among the plurality of first light emitting elements 71 and the second light emitting element 72 based on the target achievement degree evaluated by the achievement degree evaluation unit 27 and lights the light emitting elements when it is determined by the operation determination unit 28 that there is an operation of instructing a report while the exercise strength described above is being reported. More specifically, the report control unit 29 lights the first light emitting element 711 when the target achievement degree is equal to or more than 20% and less than 40%. In addition, the report control unit 29 lights the first light emitting elements 711 and 712 when the target achievement degree is equal to or more than 40% and less than 60%. The report control unit 29 lights the first light emitting elements 711, 712, and 713 when the target achievement degree is equal to or more than 60% and less than 80%. Furthermore, the report control unit 29 lights all of the first light emitting elements 711, 712, 713 and 714 when the target achievement degree is equal to or more than 80% and less than 100%. In addition, the report control unit 29 lights the plurality of first light emitting elements 71 and the second light emitting element 72 when the target achievement degree is equal to or more 100%. In addition, when the target achievement degree is less than 20%, an extinction state of all of the plurality of first light emitting elements 71 and the second light emitting element 72 is maintained.

In other words, the report control unit 29 increases the number of the first light emitting elements 712, 713 and 714 that enter a blinking state gradually from the first light emitting element 711 arranged in the position farthest from the second light emitting element 72 each time the target achievement degree exceeds a predetermined ratio. Thus, since the number of the first light emitting elements 71 controlled to be in the lighting state gradually increases as the target achievement degree increases, the target achievement degree can be recognized in a sense by viewing a so-called digital level indication meter.

In addition, the information reported by the report control unit 29 is not limited to the exercise strength and the target achievement degree. In the embodiment, when the USB terminal portion 8 of the biological information measurement device 1 is connected to the cradle 9 and charging is started, the second light emitting element 72 is lit.

In addition, the report control unit 29 executes various processes of display on the display unit 4. For example, the report control unit 29 has a function of displaying information such as a message for urging charging of the biological information measurement device 1 when it is determined by the charge amount determination unit 33, which will be described below, that the charge amount of the battery 13 is less than a predetermined charge amount.

The connection determination unit 30 determines whether the connection has been released after the USB terminal portion 8 as the connection portion of the biological information measurement device 1 has been connected with the terminal portion 94 of the cradle 9. The initial start-up unit 31 has a function of initially starting up various systems that are controlled by the control unit 20. In addition, the resetting unit 32 has a function of causing the initial start-up unit 31 to initially start up various systems when it is determined by the connection determination unit 30 that the connection has been released after the USB terminal portion 8 of the biological information measurement device 1 has been connected with the terminal portion 94 of the cradle 9. The charge amount determination unit 33 has a function of detecting a charge amount of the battery 13 and determining whether the charge amount is less than the predetermined charge amount (for example, half of a maximum charge amount).

Entire Configuration of the Cradle

Figure 5:
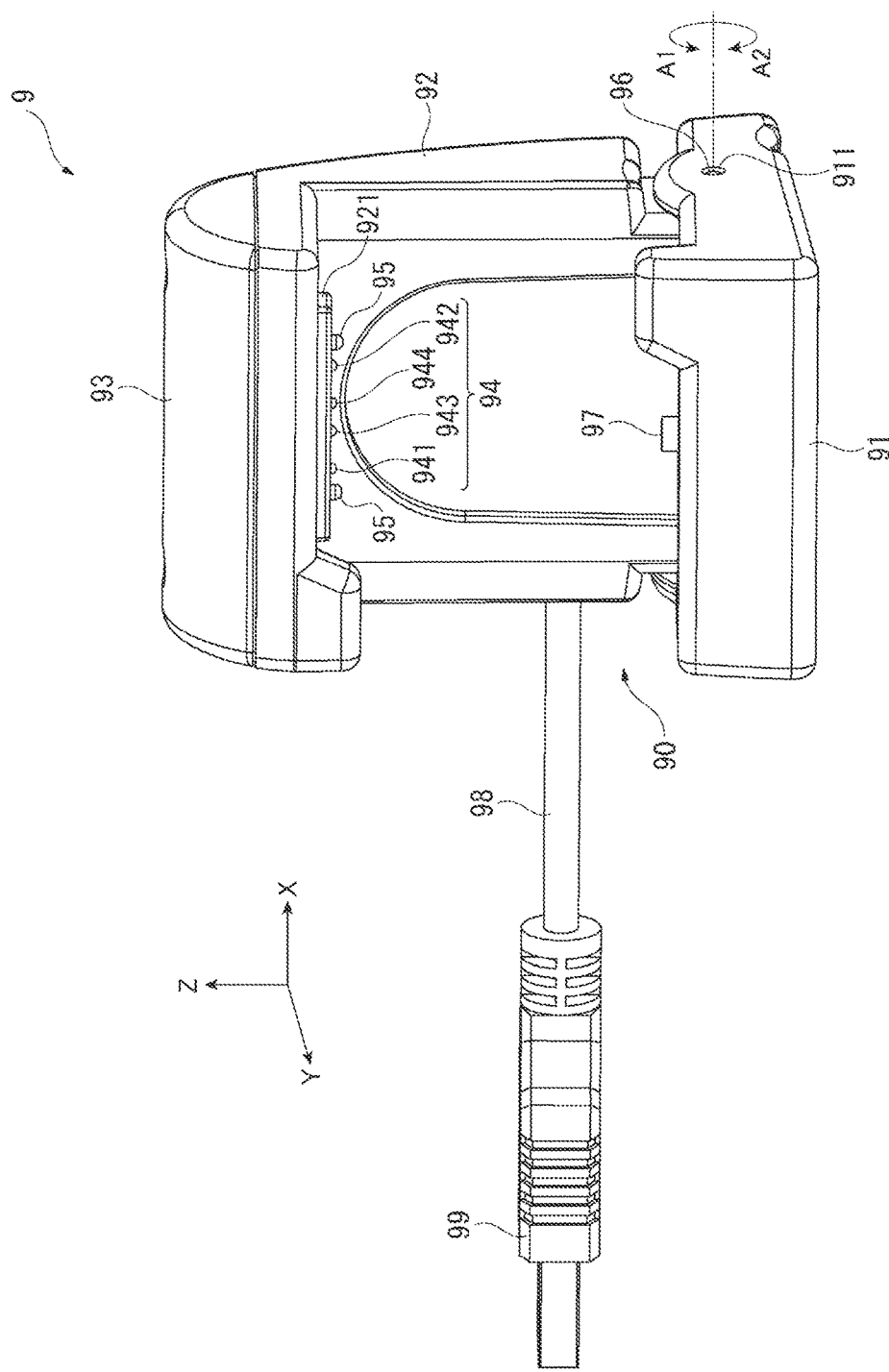
FIG. 5 is a perspective view of a cradle to which the biological information measurement device of the embodiment is attached when viewed from a front side.

FIG. 5 is a perspective view of the cradle 9 to which the biological information measurement device 1 is attached when viewed from the front side.

The cradle 9 is connected to another electronic device (for example, a personal computer or a smartphone) used integrally with the cradle 9, and has a function of charging the biological information measurement device 1, and a function of transferring predetermined information (for example, exercise strength and a target achievement degree) acquired from the biological information measurement device 1 to the other electronic device.

The cradle 9 includes a lower case 91, a middle case 92, and an upper case 93, as illustrated in FIG. 5. The lower case 91 serves as a pedestal installed on an installation surface. The lower case 91 includes a hole portion 911 that penetrates the lower case 91 in a width direction (X direction).

A movable shaft portion 96 is inserted into the hole portion 911 via the middle case 92. Accordingly, the middle case 92 is attached to the lower case 91 to be rotatable in a direction indicated by an arrow A.

The middle case 92 is formed in a reverse L shape extending in a vertical direction (Z direction) from the lower case 91 and also extending to a front side (Y direction) from an upper portion. In addition, a spring member (not illustrated) is connected to the movable shaft portion 96, and biases the middle case 92 in a direction indicated by an arrow A1. Accordingly, the middle case 92 is adapted to automatically return in the direction indicated by the arrow A1 even when the middle case 92 is rotated in a direction indicated by an arrow A2.

The upper case 93 is a cover that covers an upper surface and a back surface of the middle case 92.

With the configuration as described above, the cradle 9 forms a recessed portion 90 having a U-shape. A base portion 921 is formed on an upper end portion of the recessed portion 90, that is, a lower surface of a projecting portion of the middle case 92. A plurality of hole portions into which the terminal portion 94 described above is inserted are formed in this base portion 921. The terminal portion 94 of the cradle 9 includes the $V_{BUS}$ terminal 941, the GND terminal 942, the D+ terminal 943 and the D− terminal 944. This terminal portion 94 is arranged in the middle case 92, and a distal end thereof is projected from the hole portion (not illustrated) of the base portion 921. In addition, positioning projections 95 are formed in both ends of the terminal portion 94 projecting from the base portion 921. The positioning projections 95 have shapes fitted to the positioning holes 63 provided in the device body 2 of the biological information measurement device 1 described above.

In addition, a rubbery projection 97 is provided in a lower end portion of the recessed portion 90, that is, on a surface in the X direction of the lower case 91. This rubbery projection 97 is formed in a size fitting between the operation units 5 provided in the device body 2 of the biological information measurement device 1 described above.

In addition, a USB cable 98 is connected to the middle case 92. A USB terminal 99 is formed in a distal end of the USB cable 98, and can be connected to another electronic device (for example, a personal computer). The USB terminal 99 includes four terminals (pins), and the respective terminals are electrically connected to four terminals of the terminal portion 94 via the USB cable 98. Accordingly, for example, the USB terminal 99 of the cradle 9 is connected to the other electronic device, such that power supplied from the other electronic device via the USB cable 98 can be supplied to the $V_{BUS}$ terminal 941 and the GND terminal 942 of the terminal portion 94. In addition, via the D+ terminal 943 and the D− terminal 944 of the terminal portion 94, predetermined information from the biological information measurement device 1 attached to the cradle 9 can be acquired or information from the other electronic device can be provided to the biological information measurement device 1.

Figure 6:
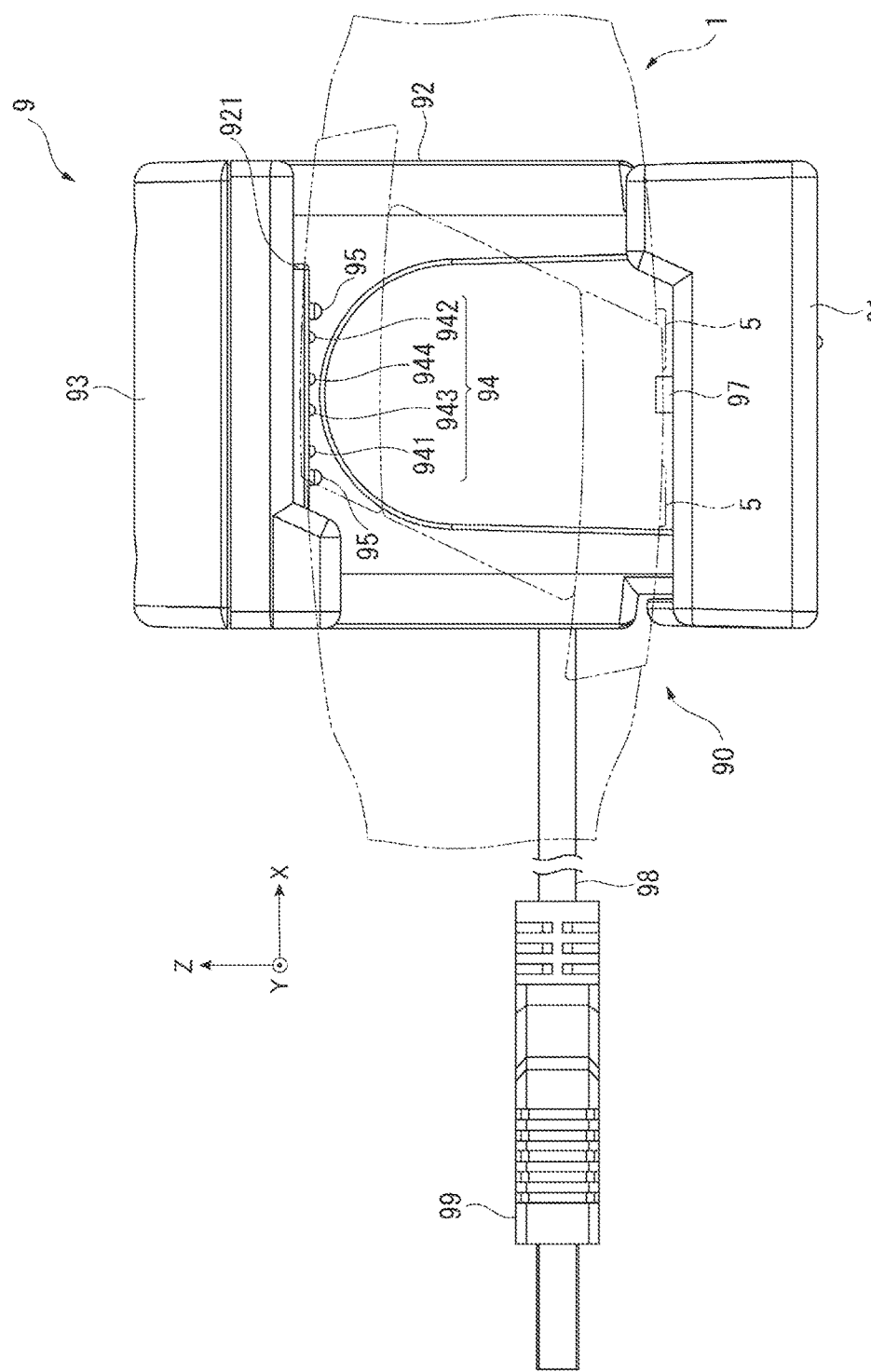
FIG. 6 is a front view illustrating a state in which the biological information measurement device of the embodiment is attached to a cradle.
Figure 7:
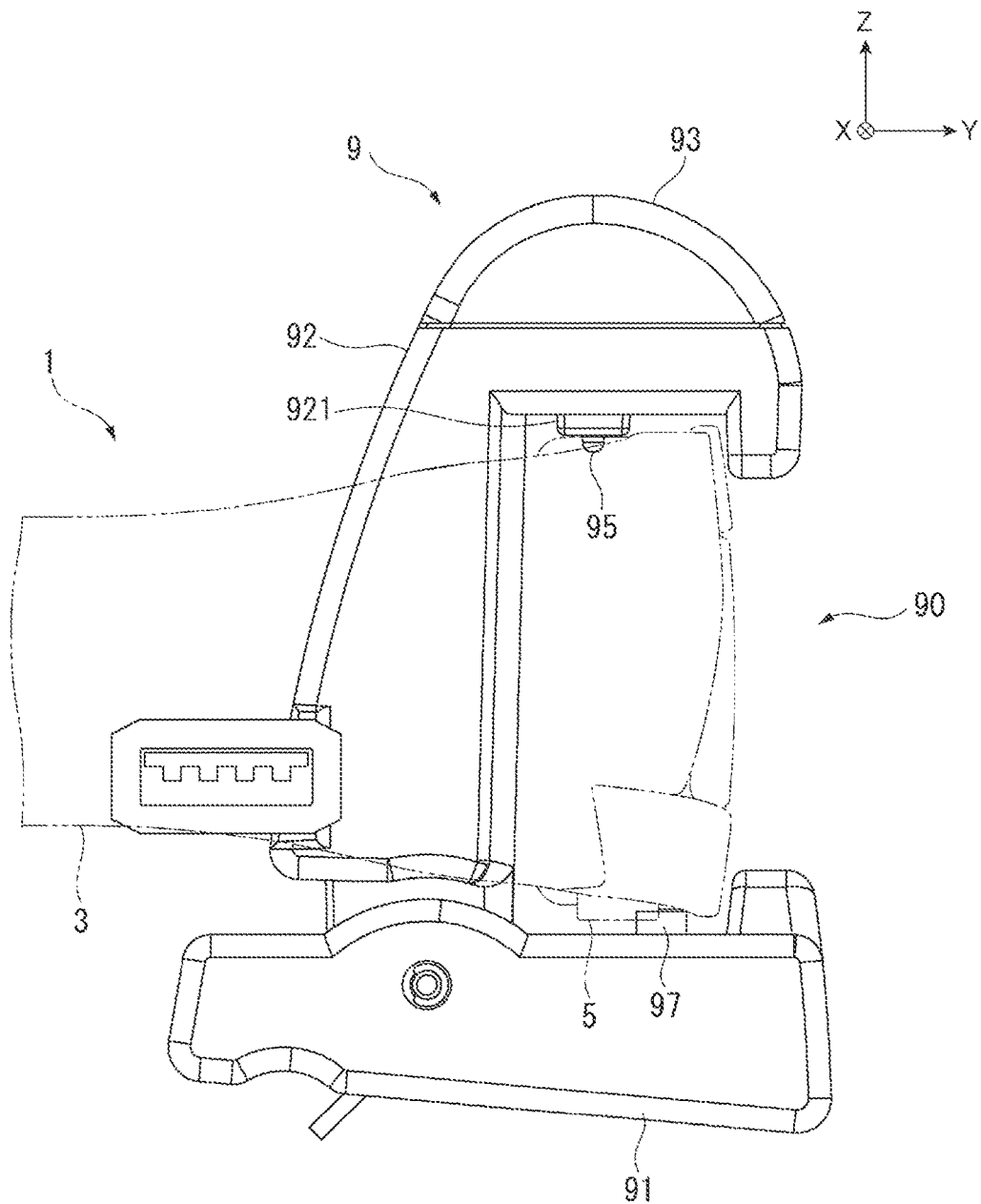
FIG. 7 is a side view illustrating a state in which the biological information measurement device of the embodiment is attached to a cradle.

Method of Attaching or Detaching the Biological Information Measurement Device to or from the Cradle FIG. 6 is a front view illustrating a state in which the biological information measurement device 1 is attached to the cradle 9. FIG. 7 is a side view illustrating a state in which the biological information measurement device 1 is attached to the cradle 9.

The biological information measurement device 1 is attached to the cradle 9, as illustrated in FIGS. 6 and 7.

First, the user operates to rotate the middle case 92 of the cradle 9 in the direction indicated by the arrow A2. Accordingly, an opening of the recessed portion 90 of the cradle 9 becomes large, making it easy to attach the biological information measurement device 1 to the cradle 9. Also, the user fits the positioning projections 95 of the cradle 9 to the positioning holes 63 provided in the side surface of the device body 2 of the biological information measurement device 1. Accordingly, the terminal portion 94 of the cradle 9 is connected to the USB terminal portion 8. Specifically, the $V_{BUS}$ terminal 941, the GND terminal 942, the D+ terminal 943 and the D− terminal 944 of the cradle 9 are connected to the $V_{BUS}$ terminal 81, the GND terminal 82, the D+ terminal 83 and the D− terminal 84 of the USB terminal portion 8 provided on the side surface of the device body 2, respectively.

Also, when the user confirms the connection of the terminals, the user takes his or her hand off the middle case 92. Accordingly, the middle case 92 enters a state illustrated in FIGS. 6 and 7 due to a biasing force of the spring member (not illustrated) provided in the middle case 92. In this case, the rubbery projection 97 is fitted between the operation units 5 provided in the side surface of the biological information measurement device 1 and the biological information measurement device 1 is supported. In other words, the side surface in the X direction of the biological information measurement device 1 is biased by the positioning projections 95 and the side surface on an opposite side in the X direction is biased by the rubbery projection 97. Accordingly, the terminal portion 94 of the cradle 9 and the USB terminal portion 8 of the biological information measurement device 1 are reliably connected.

System Resetting Process of the Biological Information Measurement Device

Next, the system resetting process using the biological information measurement device 1 as described above will be described based on the drawings.

Figure 8:
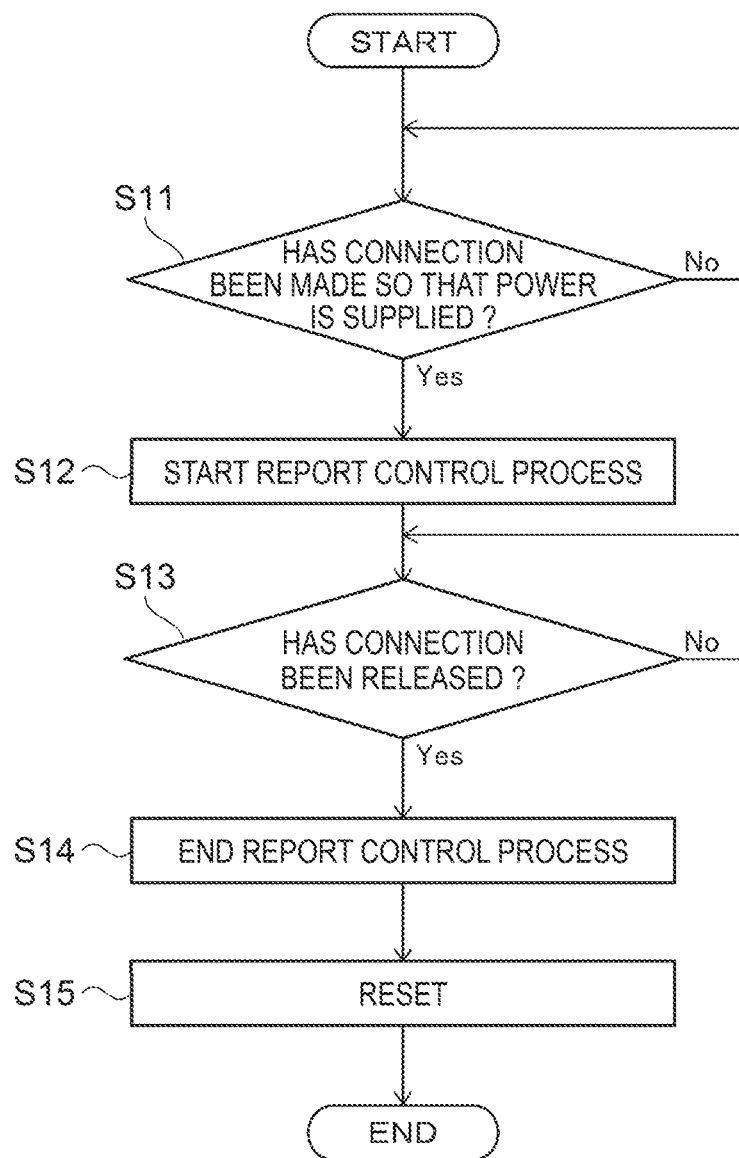
FIG. 8 is a flowchart of a system resetting process using the biological information measurement device of the embodiment.

FIG. 8 is a flowchart of the system resetting process using the biological information measurement device.

In the system resetting process by the biological information measurement device 1, the connection determination unit 30 determines whether connection has been made in a state in which power supply to the battery 13 of the biological information measurement device 1 is possible, as illustrated in FIG. 8 (S11). Specifically, the connection determination unit 30 determines whether the $V_{BUS}$ terminal 81 of the biological information measurement device 1 and the $V_{BUS}$ terminal 941 of the cradle 9 are connected and an electric potential of the $V_{BUS}$ terminal 81 of the USB terminal portion 8 has increased. In this case, when the cradle 9 is connected to another electronic device (for example, a personal computer) and power is supplied from the other electronic device via the USB cable 98, the electric potential of the $V_{BUS}$ terminal 81 connected to the $V_{BUS}$ terminal 941 increases. Accordingly, when it is determined that the connection has been made in a state in which power supply to the battery 13 of the biological information measurement device 1 is possible (YES in S11), the report control unit 29 starts a report control process (S12). Specifically, the report control unit 29 lights the second light emitting element 72 of the LED light source unit 7. Accordingly, the user can recognize that the biological information measurement device 1 is in a charging state.

On the other hand, even when the $V_{BUS}$ terminal 81 of the USB terminal portion 8 and the $V_{BUS}$ terminal 941 of the terminal portion 94 of the cradle 9 are connected, power is not supplied to the cradle 9 and the electric potential of the $V_{BUS}$ terminal 81 does not increase if the cradle 9 is not connected to the other electronic device (NO in S11). Accordingly, the process of step S11 is repeated until the power is supplied to the cradle 9.

Also, the connection determination unit 30 determines whether the power supply to the battery 13 of the biological information measurement device 1 has stopped (S13). Specifically, the connection determination unit 30 determines whether the electric potential of the $V_{BUS}$ terminal 81 of the USB terminal portion 8 has decreased. The case in which the electric potential of the $V_{BUS}$ terminal 81 of this USB terminal portion 8 has decreased may include the case in which connection between the $V_{BUS}$ terminal 941 of the cradle 9 and the $V_{BUS}$ terminal 81 has been released or the USB terminal 99 of the cradle 9 has been withdrawn from the other electronic device (for example, a personal computer) and power from the other electronic device has not been supplied to the cradle 9. Accordingly, when it is determined in step S13 that the power supply to the battery 13 of the biological information measurement device 1 has stopped (YES in S13), the report control unit 29 ends the report control process (S14). Specifically, the report control unit 29 stops lighting of the second light emitting element 72 of the LED light source unit 7. Also, the resetting unit 32 causes the initial start-up unit 31 initially starting up the biological information measurement device 1 to initially start up the biological information measurement device 1, to execute the system resetting process (S15).

Specifically, the resetting unit 32 starts up the initial start-up unit 31 and executes resetting of the entire system controlled by the control unit 20, that is, power-on resetting.

Thus, when the resetting process by the resetting unit 32 is completed, the system resetting process is completed.

Operation and Effects of the Embodiment

In the embodiment, when the biological information measurement device 1 is removed from the cradle 9 to release the connection between the terminal portion 94 and the USB terminal portion 8 after the terminal portion 94 of the cradle 9 is connected to the USB terminal portion 8, the resetting unit 32 starts up the initial start-up unit 31 to initially start up the biological information measurement device 1.

Accordingly, since initialization (system resetting) of the biological information measurement device 1 is executed by simply removing the biological information measurement device 1 from the cradle 9, the system resetting can be automatically executed even when the user does not perform a system resetting operation. Therefore, the biological information measurement device 1 can be periodically subjected to the system resetting, thus improving stability of the system in comparison with the case in which the system resetting is not executed for a long period of time.

In the embodiment, a change in the voltage or the current applied to the $V_{BUS}$ terminal 81 is detected to determine whether the connection of the $V_{BUS}$ terminal 941 of the cradle 9 to the $V_{BUS}$ terminal 81 has been released. Thus, when the change in the voltage or the current applied to the $V_{BUS}$ terminal 81 is detected to automatically perform system resetting, system resetting can be executed each time the biological information measurement device 1 is charged. In other words, since charging of the battery 13 of the biological information measurement device 1 is necessarily performed, the user removes the biological information measurement device 1 from the cradle 9 when the biological information measurement device 1 is set in (attached to) the cradle 9 and charging is completed. Therefore, the system resetting can be automatically executed at the time of a charging task that is performed on a daily basis even when the user does not perform the system resetting operation.

In the embodiment, the exercise strength acquisition and determination unit 22 determines the pulse zone (the first to fourth zones) to which the exercise strength corresponding to the pulse rate acquired by the pulse acquisition unit 21 belongs, and the report control unit 29 controls the lighting state of the LED light source unit 7 to report the determined zone.

Therefore, the user can easily recognize the zone to which the current exercise strength belongs, based on the lighting state of the plurality of first light emitting elements 711, 712, 713 and 714. Particularly, since the number of the first light emitting elements 71 that are lit changes according to levels of the first to fourth zones, it is possible to easily recognize the zone to which the exercise strength belongs. In addition, since the lighting state of the LED light source unit 7 is controlled to perform reporting, the user can reliably recognize the determined pulse zone even at night.

Accordingly, since the user can recognize the zone to which the current exercise strength belongs based on the lighting state of the LED light source unit 7, it is possible to easily make a determination as to whether the current exercise strength is to be maintained or changed.

Further, when the biological information measurement device 1 is attached to the cradle 9, the D+ terminal 83 and D− terminal 84 that constitute the information exchange connection portion and the D+ terminal 943 and the D− terminal 944 of the cradle 9 are also connected, various information including measurement data such as the pulse rate or the exercise evaluation amount or set data of the pulse zone or the target value can be communicated with the other electronic device (for example, a personal computer) via the cradle 9 at the same time as charging. Therefore, the measurement data can be analyzed in detail in the personal computer or the like. In addition, the pulse zone, the target value and the like can be set and set data can be transmitted to the biological information measurement device 1 via the cradle 9. Therefore, it is unnecessary to perform a task of setting the pulse zone, the target value and the like in the portable electronic device, and it is possible to reduce a burden of tasks of the user.

In the embodiment, since the exercise evaluation amount measurement unit (the calorie calculation unit 24, the exercise time measurement unit 25, and the step number measurement unit 26), the achievement degree evaluation unit 27 that evaluates the achievement degree (target achievement degree), and the report control unit 29 that controls the LED light source unit 7 to report the target achievement degree are included, the user can easily recognize the target achievement degree with respect to the target value of the exercise evaluation amount (the number of steps, the exercise time, and the calorie consumption amount) from the lighting state of the LED light source unit 7.

In addition, reporting of the zone to which the pulse rate corresponds, that is, the exercise strength, and reporting of the target achievement degree of various exercise evaluation amounts can be switched and displayed by controlling the lighting state of the LED light source unit 7. Therefore, the user can exercise while confirming a change in a real-time pulse rate (exercise strength), and can immediately confirm the achievement degree by performing a tapping operation when the user wants to confirm the achievement degree. Therefore, it is possible to perform efficient exercise support.

In addition, since the reporting of the exercise strength (the pulse rate) is performed through blinking of the light emitting elements 71 and 72 and the reporting of the target achievement degree is performed through lighting of the light emitting elements 71 and 72 for a different lighting pattern, the user can easily recognize whether the currently reported information is the exercise strength or the target achievement degree.

Besides, the display can be switched to the display of the target achievement degree by performing a tapping operation during the report of the exercise strength. The operability of the user can be improved since the display automatically returns to the report of the exercise strength when the display of the target achievement degree is performed for a certain period of time (for example, 5 seconds).

In the embodiment, it is possible to easily recognize that the biological information measurement device 1 is being charged since the second light emitting element 72 is lit while power supplied from the terminal portion 94 of the cradle 9 via the USB terminal portion 8 is being supplied to the battery 13, i.e., during charging of the battery 13. In addition, the user can recognize that the biological information measurement device 1 cannot be charged and, for example, that the cradle 9 is not connected to the other electronic device (for example, a personal computer) via the USB terminal 99 when the second light emitting element 72 is not lit even though the $V_{BUS}$ terminal 81 of the USB terminal portion 8 and the $V_{BUS}$ terminal 941 of the terminal portion 94 are connected. Therefore, it is possible to reliably charge the portable electronic device.

In the embodiment, when it is determined by the charge amount determination unit 33 that the charge amount of the battery 13 is less than a predetermined charge amount (a half of a maximum charge amount), the report control unit 29 displays information for urging charging on the display unit 4. Thus, it is possible to urge the user to charge the biological information measurement device 1. Accordingly, since the user is able to charge the biological information measurement device 1 more reliably, the system resetting is automatically achieved each time the charging is performed, and the stability of the system can be further maintained.

Modification Example

Further, the invention is not limited to the above-described embodiment, and modifications and improvements in the range that can achieve the object of the invention are included in the invention.

In the embodiment, the connection determination unit 30 determines whether the connection between the USB terminal portion 8 and the terminal portion 94 of the cradle 9 has been released based on the electric potential of the $V_{BUS}$ terminal 81 of the USB terminal portion 8, but the invention is not limited thereto.

For example, the connection determination unit 30 may determine whether the D+ terminal 83 and the D− terminal 84 of the USB terminal portion 8 and the D+ terminal 943 and the D− terminal 944 of the terminal portion 94 of the cradle 9 have been connected and, for example, exchange (transmission) of various information (for example, the information on the exercise strength or the target achievement degree) has been performed. Accordingly, when the communication cannot be performed after the communication process with the other electronic device (for example, a personal computer) connected to the cradle 9 has been successful as a result of the communication process via the D+ terminal 83 and the D− terminal 84, it can be determined that the connection of the D+ terminal 83 and the D− terminal 84 connected to the D+ terminal 943 and the D− terminal 944 of the terminal portion 94 of the cradle 9 has been released. In this case, even when a charging connection terminal is not provided in the cradle 9, it can be determined that the connection has been released.

In other words, when the biological information measurement device 1 is removed from the cradle 9 after the biological information measurement device 1 has been attached to the cradle 9 and the exchange of various information has been performed, the initial start-up unit 31 is started by the resetting unit 32 and the biological information measurement device 1 is initially started up.

In addition, the connection determination unit 30 may detect that the positioning projections 95 of the cradle 9 have been fitted to the positioning holes 63 of the biological information measurement device 1 and the fitting has been released. Accordingly, when the biological information measurement device 1 is attached to the cradle 9 and then removed, the initial start-up unit 31 may be started up by the resetting unit 32 to initially start up the biological information measurement device 1. In other words, the connection determination unit 30 may detect that the biological information measurement device 1 is attached to the cradle 9 and then removed using any means.

Further, the report control unit 29 lights the second light emitting element 72 when charging is started (when charging is being performed) in the embodiment. It is understood that any one of the plurality of first light emitting elements 71 may be lit or all of the plurality of first light emitting elements 71 may be lit. In other words, when it is reported to the user that the biological information measurement device 1 is being charged, any one light emitting element of the LED light source unit 7 may be lit.

In addition, the report control unit 29 may report that the communication process has been performed, by controlling the lighting state of the LED light source unit 7 while the communication process is being performed via the D+ terminal 83 and the D− terminal 84 of the USB terminal portion 8.

For example, when the D+ terminal 83 and the D− terminal 84 of the USB terminal portion 8 and the D+ terminal 943 and the D− terminal 944 of the terminal portion 94 of the cradle 9 are connected and the communication process is started, the report control unit 29 may sequentially light the first light emitting elements 71 in order of the first light emitting element 711, the first light emitting element 712, the first light emitting element 713, and the first light emitting element 714. In addition, in this case, when all of the plurality of first light emitting elements 71 enter a lighting state, all the first light emitting elements 71 may be in an extinction state and lit sequentially from the first light emitting element 711 again. The lighting control thereof may be repeated until the communication process is completed.

In addition, the report control unit 29 may blink the first light emitting element 711 once, blink the first light emitting element 712 once, blink the first light emitting element 713 once, and then blink the last first light emitting element 714 once. Even in this case, the first light emitting element 711 may blink after the last first light emitting element 714 blinks, to repeat the lighting control until the communication process is completed. Accordingly, the user can recognize that the communication process is performed and that the communication process is completed.

In addition, the report control unit 29 may display a button for selection of whether or not to start the communication process on a screen of the other electronic device (for example, a personal computer) connected to the cradle 9 when the D+ terminal 83 and the D− terminal 84 of the USB terminal portion 8 and the D+ terminal 943 and the D− terminal 944 of the terminal portion 94 of the cradle 9 are connected. In addition, such a button for selection of whether or not to start the communication process may be displayed on the display unit 4 of the biological information measurement device 1. Accordingly, the user can recognize that the D+ terminal 83 and the D− terminal 84 of the USB terminal portion 8 and the D+ terminal 943 and the D− terminal 944 of the terminal portion 94 of the cradle 9 have been reliably connected, and start the communication process smoothly.

In addition, in the embodiment, while the biological information measurement device 1 includes the report control unit 29, the report control unit 29 may not be provided. In other words, any portable electronic device may be used as long as the portable electronic device includes the connection determination unit 30, the initial start-up unit 31, and the resetting unit 32.

In addition, the shape of the cradle 9 is not limited to the embodiment. In other words, any shape may be used as long as the biological information measurement device 1 can be attached thereto. In addition, while the USB terminal 99 of the cradle 9 is an example of a standard A plug, for example, the USB terminal 99 may be a standard B plug or may be a mini-B plug. Accordingly, the cradle 9 may be connected to, for example, a smartphone, in addition to a personal computer.

Further, the shape of the biological information measurement device 1 is not limited to the embodiment. In other words, in the embodiment, while the biological information measurement device 1 includes the band 3 and is wound around the wrist and used, the invention is not limited thereto. For example, the biological information measurement device 1 may be an electronic device capable of being carried, such as a smartphone, irrespective of its shape.

The entire disclosure of Japanese Patent Application No. 2013-213397, filed Oct. 11, 2013 is expressly incorporated by reference herein.

What is claimed is:

1. A portable electronic device that is attachable to or detachable from a cradle, the device comprising:
   a connection portion connected to a terminal provided in the cradle;
   an initial start-up unit that initially starts up the portable electronic device;
   a connection determination unit that determines whether the connection has been released after the connection portion has been connected to the terminal of the cradle; and a resetting unit that causes the initial start-up unit to initially start up the portable electronic device, including resetting power of the device, when it is determined by the connection determination unit that the connection has been released.

2. The portable electronic device according to claim 1, further comprising:

a rechargeable battery, wherein the connection portion includes a charging connection portion that acquires power that is supplied from the cradle, and the connection determination unit detects a voltage or a current applied to the charging connection portion and determines whether the connection to the terminal of the cradle has been released.

3. The portable electronic device according to claim 1, wherein the connection portion includes an information exchange connection portion that exchanges information with another electronic device connected to the cradle via the cradle, and the connection determination unit detects a result of the information exchange via the information exchange connection portion and determines whether the connection to the terminal of the cradle has been released.

4. The portable electronic device according to claim 1, further comprising:

a display unit;

a plurality of light emitting elements;

a pulse acquisition unit that acquires a pulse rate of a subject;

a pulse zone determination unit that determines any one of a plurality of pulse zones divided in advance to which the pulse rate belongs; and a report control unit that reports the pulse zone to which the pulse rate belongs by controlling a lighting state of the plurality of light emitting elements based on a determination result of the pulse zone determination unit.

5. The portable electronic device according to claim 4, further comprising:

an exercise evaluation amount measurement unit that measures an exercise evaluation amount for evaluating an exercise amount of the subject; and an achievement degree evaluation unit that evaluates an achievement degree of the exercise evaluation amount with respect to a target exercise value set in advance, wherein, when the pulse zone is reported, the report control unit reports the achievement degree evaluated by the achievement degree evaluation unit by controlling the lighting state of the plurality of light emitting elements when an operation of instructing a report is performed by the subject.

6. The portable electronic device according to claim 4, further comprising:

a rechargeable battery, wherein the connection portion includes a charging connection portion that acquires power supplied from the cradle, and the report control unit controls at least one of the plurality of light emitting elements to be in a lighting state when the power supplied from the cradle via the charging connection portion is supplied to the battery.

7. The portable electronic device according to claim 4, further comprising:

a rechargeable battery; and a charge amount determination unit that determines whether a charge amount of the battery is less than a predetermined charge amount, wherein the report control unit causes the display unit to display information for urging charging when it is determined by the charge amount determination unit that the charge amount of the battery is less than the predetermined charge amount.

* * * * *